United States Patent [19]

Ray

[11] Patent Number: 4,613,693

[45] Date of Patent: Sep. 23, 1986

[54] PROCESS FOR THE CO-PRODUCTION OF A $C_2$ TO $C_{10}$ MONOCARBOXYLIC ACID AND FORMIC ACID

[75] Inventor: David J. M. Ray, Hull, England

[73] Assignee: BP Chemicals Limited, London, England

[21] Appl. No.: 357,186

[22] Filed: Mar. 11, 1982

[30] Foreign Application Priority Data

Mar. 13, 1981 [GB] United Kingdom ................ 8107943

[51] Int. Cl.$^4$ ...................... C07C 51/12; C07C 53/04; C07C 53/08
[52] U.S. Cl. .................................... 562/517; 260/413; 560/232; 562/606; 562/607; 562/609
[58] Field of Search ................ 560/232; 562/606, 517, 562/607, 609; 260/413

[56] References Cited

FOREIGN PATENT DOCUMENTS 1286224 8/1972 United Kingdom ................ 562/607

Primary Examiner—Vivian Garner
Attorney, Agent, or Firm—Brooks Haidt Haffner & Delahunty

[57] ABSTRACT $C_2$ to $C_{10}$ monocarboxylic acids are co-produced with formic acid by reacting at an elevated temperature below 250° C. a $C_1$ to $C_9$ alkyl formate with carbon monoxide and water in the presence as catalyst of a Group VIII noble metal component and an iodine or bromine-containing promoter, the partial pressure of carbon monoxide being in the range 1 to 300 bar, the concentration of noble metal component being in the range from 100 to 5000 ppm and the atomic ratio of noble metal to iodine or bromine being in the range from 1:50 to 1:1000 and thereafter recovering the co-produced $C_2$ to $C_{10}$ monocarboxylic acid and formic acid. In a preferred embodiment, the alkyl formate is methyl formate and the recovered acids are acetic acid and formic acid.

9 Claims, No Drawings

PROCESS FOR THE CO-PRODUCTION OF A $C_2$ TO $C_{10}$ MONOCARBOXYLIC ACID AND FORMIC ACID

The present invention relates to a process for the co-production of a $C_2$ to $C_{10}$ monocarboxylic acid and formic acid by the carbonylation of a $C_1$ to $C_9$ alkyl formate and in particular to the co-production of acetic acid and formic acid by the carbonylation of methyl formate.

The carbonylation of olefins, alcohols and ester, halide or ether derivatives of the alcohols under relatively mild conditions in the presence of homogeneous catalyst systems containing a Group VIII noble metal, such as rhodium or iridium, and iodine or bromine, has been known for some time and is described in a large number of patent specifications such as British Pat. Nos. 1233121; 1234641; 1253758; 1277242 and 1355146 to name but a few. In particular British Pat. No. 1233121 describes and claims a process for the treatment of a reactant which is an alkyl compound having n carbon atoms, where n is a number from 1 to 20, the said reactant being an alcohol, halide or ester, to obtain a mixture comprising an organic acid having n+1 carbon atoms, or an ester of the alcohol having n carbon atoms with the said acid. British Pat. No. 1276326 describes and claims a process for the production of a monocarboxylic acid or ester thereof which comprises reacting with carbon monoxide, in the presence of a catalyst, at 125° to 250° C., a feedstock which is an alcohol of the formula $RCH_2OH$ or halide of the formula $RCH_2Hal$ where Hal is chlorine, bromine or iodine, where R represents phenyl, alkylphenyl, alpha-hydroxyalkyl, etherified alpha-hydroxyalkyl, or alpha-haloalkyl or an ether derivative of said alcohol or an ester derivative of said alcohol wherein the acid moiety contains 1 to 20 carbon atoms. Whilst the foregoing specifications envisage the use of esters, including formate esters, the product obtained from the process described in GB No. 1233121 is a monocarboxylic acid containing n+1 carbon atoms which does not include formic acid and GB 1276326 does not cover the use of alkyl formates such as methyl formate.

In other publications in which formate esters and specifically methyl formate are reacted in the presence of carbon monoxide the objective is to achieve isomerisation and not carbonylation of the ester and to further this end the system contains little or no added water. Thus British Pat. No. 1286224 describes the isomerisation of methyl formate to acetic acid using rhodium catalysts, e.g. $Rh(CO)Cl(PPn_3)_2$ in the presence of methyl iodide. High yields of acetic acid with no co-product formic acid are claimed for anhydrous homogeneous systems at 200° C. and 50 bar initial carbon monoxide pressure. U.S. Pat. No. 4,194,056 describes a similar reaction in which acetic acid is the sole product.

It has now been unexpectedly found that a $C_2$ to $C_{10}$ monocarboxylic acid and formic acid can be co-produced by the carbonylation of a $C_1$ to $C_9$ alkyl formate in the presence of homogeneous catalyst systems containing a Group VIII noble metal, e.g. rhodium, and iodine or bromine as promoter under a particular set of reaction conditions. This is all the more surprising in view of an article in Chemical Communications, 1971, page 1072, describing the decomposition of 70% aqueous formic acid at 100° C. by rhodium and hydrogen iodide involving decarboxylation and decarbonylation mechanisms and by hydrogen iodide via decarbonylation.

Accordingly the present invention provides a process for the co-production of a $C_2$ to $C_{10}$ monocarboxylic acid and formic acid which process comprises reacting at an elevated temperature below 250° C. a $C_1$ to $C_9$ alkyl formate with carbon monoxide and water in the presence as catalyst of a Group VIII noble metal component and an iodine or bromine-containing promoter, the partial pressure of carbon monoxide being in the range 1 to 300 bar, the concentration of noble metal component being in the range from 100 to 5000 ppm and the atomic ratio of noble metal to iodine or bromine being in the range from 1:50 to 1:1000 and thereafter recovering the co-produced $C_2$ to $C_{10}$ monocarboxylic acid and formic acid.

Of the $C_1$ to $C_9$ alkyl formates which may be used in the process of the invention methyl formate, ethyl formate, propyl formate and butyl formate are preferred and methyl formate is particularly preferred. The products from the reaction of methyl formate with carbon monoxide and water are acetic acid and formic acid. Ethyl formate produces propionic acid and formic acid. Mixtures of the alkyl formates resulting in the formation of a mixed monocarboxylic acid product containing formic acid may also be used if so desired. The ratio of formic acid to other monocarboxylic acids in the product may also be adjusted by the addition of an alkanol, to the reactants. For example by the addition of methanol to the reaction of methyl formate, water and carbon monoxide the ratio of formic acid to acetic acid in the product may be adjusted.

The carbon monoxide is preferably substantially pure, though carbon monoxide streams containing inert impurities such as carbon dioxide, methane, nitrogen, noble gases and paraffinic hydrocarbons having 2 to 4 carbon atoms may be employed. However when inert impurities are present total reactor pressure should be increased to maintain a desired carbon monoxide partial pressure. Hydrogen may also be present in the carbon monoxide either as an impurity or by deliberate addition if so desired. The concentration of carbon monoxide in the feed gas mixture is suitably from 1 vol percent to 99.9 vol percent, preferably from 10 vol percent to 99.9 vol percent.

As mentioned hereinbefore the catalyst as charged is a Group VIII noble metal component. Suitably the Group VIII noble metal component may be rhodium, iridium, platinum, palladium, ruthenium or osmium, preferably rhodium or iridium, even more preferably rhodium. The metal component may suitably be the elemental metal or a compound containing the metal, such as an oxide, a salt, an organometallic compound or a coordination compound. Preferred compounds include the metal halides, carbonyls and carboxylates, e.g. $RhCl_3$, $RhBr_3$, $RhI_3$, $Rh$ $(acetate)_2$, $Rh_4(CO)_{12}$, $Rh_2(CO)_4I_2$, $Ir_4(CO)_{12}$, $Ir_2(CO)_4I_2$, $IrCl_3$, $IrBr_3$ and $IrI_3$.

The iodine or bromine-containing promoter may suitably be iodine or bromine and/or an iodine or bromine compound. Suitable compounds include alkyl iodides or bromides, e.g. methyl iodide, methyl bromide, ethyl iodide or ethyl bromide, quaternary iodides or bromides, such as quaternary ammonium iodides or bromides, metal iodides or bromides or hydrogen iodide or bromide. With regard to alkyl iodides and bromides it is particularly preferred to employ an alkyl iodide or bromide having an alkyl group identical to the alkyl moiety of the ester reactant. Of the iodine or bromine-containing promoters it is preferred to use an iodine-containing promoter. Alkyl iodides and hydrogen iodide, either individually or in combination, are particularly preferred. For the carbonylation of methyl formate it is preferred to employ methyl iodide and/or hydrogen iodide as promoter.

There may also be employed a solvent which is compatible with the catalyst. A preferred solvent is a monocarboxylic acid having 2 to 20 carbon atoms, e.g. acetic, propionic, hexanoic or decanoic acid. Preferably the solvent is identical to the monocarboxylic acid produced in the reaction. For example in the reaction of methyl formate with carbon monoxide and water the solvent is preferably acetic acid. Furthermore, additives such as suitable nitrogencontaining compounds, organo-phosphines, organo-arsines and/or organo-stibines may be present if so desired. The additive may suitably be a trialkylphosphine, e.g. tri-n-butylphosphine, a triarylphosphine, e.g. triphenylphosphine, a trialkylamine, e.g. triethylamine or a heterocyclic nitrogen compound.

The partial pressure of carbon monoxide is preferably in the range from 10 to 40 bar. With regard to the ratio of reactants, although the molar ratio of water to alkyl formate may be less than 1:1 if so desired, suitably this ratio is in the range 1:1 to 10:1 and is preferably in the range 1:1 to 5:1. The concentration of the noble metal compound forming the active component of the catalyst is preferably in the range from 300 to 1000 ppm. The atomic ratio of noble metal to iodine or bromine is preferably in the range from 1:75 to 1:500. In order to optimise the yield of formic acid it is preferred to operate at less than stoichiometric conversion of the alkyl formate to carbonylation products, suitably at less than 95%, preferably at less than 90% conversion. In the particular case of methyl formate carbonylation it is generally possible to recover formic acid in greater than 90% yield when operating at 90% conversion or below.

The process may suitably be carried out by reacting the alkyl formate with carbon monoxide and water in the presence of catalyst and promoter in the liquid phase or in the vapour phase by passing alkyl formate, carbon monoxide, water and, optionally, promoter over a supported catalyst and, optionally, promoter. Any inert material may be used as support in the vapour phase process. Furthermore the reaction may be carried out batchwise or continuously, preferably continuously. Procedures for operating this type of liquid phase and vapour phase processes, both batchwise and continuously, are well known in the art and require no further elaboration.

Whether the process is carried out in the liquid phase or the vapour phase similar elevated temperatures up to 250° C., preferably within the range 140° to 200° C., are employed.

Techniques for preparing the catalyst and operating these types of liquid phase and vapour phase reactions are well known in the art as described in for example the complete specifications of British Pat. Nos. 1234641, 1277242 and 1233121.

The product recovered from the process of the present invention is a mixture of a monocarboxylic acid and formic acid. These may be separated by distillative procedures well known in the art. As hereinbefore mentioned the relative stability of the formic acid produced in the process is somewhat surprising since the expectation from the literature is that even under conditions which are relatively mild for carbonylation both rhodium and hydrogen iodide would catalyse its decomposition. It is thought that a possible explanation for the formic acid stability is that equilibrium levels of hydrogen iodide are low in the presence of excess formate ester due to the rapid forward reaction of the equilibrium:

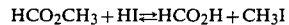

$$HCO_2CH_3 + HI \rightleftharpoons HCO_2H + CH_3I$$

and that active rhodium catalyst is tied up by the relatively rapid oxidative addition of $CH_3I$, competing with rhodium/formic acid complex formation (leading to formic acid decomposition). The other noble metals are believed to behave in a similar manner. It is not intended that the invention should be restricted in any way by the validity or otherwise of this mechanistic theory, it is merely offered as an explanation for the invention made.

The invention will now be illustrated by reference to the following examples.

EXAMPLE 1

Into an autoclave of 1 liter capacity made of a corrosion resistant material and fitted with a rotary stirrer were charged 247 g of methyl formate, 151 g of methyl iodide, 99 g of water and 1.19 g of rhodium trichloride hydrate. The autoclave was closed and carbon monoxide introduced to 17 bar pressure. The autoclave was heated to 179° C., reaction occurred and more carbon sonoxide was added to maintain the autoclave pressure at 27 bar. After 26 minutes at reaction conditions the autoclave was cooled to room temperature and the pressure released.

The liquid product was then removed from the autoclave and a small portion analysed by gas-liquid chromatography. This indicated that the reaction mixture contained the following products:- 137 g of formic acid, 78 g of methyl iodide, and 198 g of acetic acid.

EXAMPLE 2

Into the same reactor system as employed in Example 1 were charged 127 g of methyl formate, 54 g of methyl iodide, 72 g of 65% w/w aqueous hydriodic acid, 74 g of water, 0.64 g rhodium trichloride hydrate, and 179 g of propionic acid as solvent. The autoclave was closed and carbon monoxide was introduced to 17 bar pressure. The autoclave was heated to 181° C., reaction occurred and more carbon monoxide was added to maintain the pressure in the autoclave at 24 bar. After 20 minutes at reaction conditions the autoclave was cooled and the pressure released.

The liquid product was then removed from the autoclave, and a small portion analysed by gas-liquid chromatography. This indicated that the reaction mixture contained the following products: 76 g of formic acid, 43 g of methyl iodide, and 112 g of acetic acid.

EXAMPLE 3

Into the same reactor system as employed in Example 1 were charged 125 g of methyl formate, 214 g of 65% w/w aqueous hydriodic acid, 40 g of water, 0.96 g of rhodium trichloride hydrate, and 120 g of propionic acid as solvent. The autoclave was closed and carbon monoxide introduced to 17 bar pressure. The autoclave was heated to 160° C., reaction occurred and more carbon monoxide was added to maintain the pressure in the autoclave at 24 bar. After 14 minutes at reaction conditions the autoclave was cooled to room temperature and the pressure released.

The liquid product was then removed from the autoclave, and a small portion analysed by gas-liquid chromatography. This indicated that the reaction mixture contained the following products:- 81 g of formic acid, 73 g of methyl iodide, and 82 g of acetic acid.

EXAMPLE 4

Into the same reactor system as described in Example 1 were charged 151 g of methyl formate, 168 g of 65% w/w aqueous hydriodic acid, 39 g of water, 0.42 g of rhodium diacetate dimer and 145 g of propionic acid as solvent. The autoclave was closed and carbon monoxide introduced to 17 bar pressure. The autoclave was heated to 150° C., reaction occurred and more carbon monoxide was added to maintain the pressure in the autoclave at 24 bar. After 40 minutes at reaction conditions the autoclave was cooled to room temperature and the pressure released.

The liquid product was then removed from the autoclave and a small portion analysed by gas-liquid chromatography. This indicated the reaction mixture contained the following products:- 115 g of formic acid, 74 g of methyl iodide, 115 g of acetic acid, 5 g of methyl acetate, and 5 g of methyl propionate.

EXAMPLE 5

Into the reactor system described in Example 1 were charged 130 g of methyl formate, 278 g of 45% w/w hydrobromic acid in acetic acid, 100 g of water, 1.28 g of rhodium trichloride hydrate, and 71 g of propionic acid as solvent. The autoclave was closed and carbon monoxide introduced to 17 bar pressure. The autoclave was heated to 174° C., reaction occurred and carbon monoxide was added as required to maintain the pressure in the autoclave at 27 bar. After 20 minutes the autoclave was cooled and the pressure released.

The liquid product was removed from the autoclave, and a small portion analysed by gas-liquid chromatography. This indicated that the reaction mixture contained the following products:- 62 g of formic acid, 73 g of acetic acid (excluding the amount of acetic acid as co-solvent), and 2 g of methyl propionate.

EXAMPLE 6

Into the reactor system described in Example 1 were charged 84 g of methyl formate, 24 g of methanol, 215 g of 65% w/w aqueous hydriodic acid, 40 g of water, 0.96 g of rhodium trichloride hydrate, and 121 g of propionic acid as solvent. The autoclave was closed and carbon monoxide introduced to 17 bar pressure. The autoclave was heated to 146° C., reaction occurred and more carbon monoxide was added to maintain the autoclave at a constant pressure of 24 bar. After 20 minutes at reaction conditions the autoclave was cooled to room temperature and the pressure released.

The liquid product was then removed from the autoclave, and a small portion analysed by gas-liquid chromatography. This indicated that the reaction mixture contained the following products:- 52 g of formic acid, 64 g of methyl iodide, and 87 g of acetic acid.

EXAMPLE 7

In two separate experiments the autoclave was charged with 126 g of methyl formate, 94 g of 65% w/w aqueous hydriodic acid, 100 g of water, 1.28 g of rhodium trichloride hydrate and 180 g of propionic acid as solvent. The autoclave was closed and carbon monoxide introduced to 17 bar pressure. The autoclave was heated to 175° C., reaction occurred and carbon monoxide was added to maintain the pressure in the autoclave at 24 bar. In the first experiment the reaction was stopped after 20 minutes at reaction conditions and the autoclave was cooled, the pressure released and the product discharged. Analysis of a portion of the reaction solution by gas-liquid chromatography indicated that the following products were present:-80 g of formic acid, 9 g of methyl iodide, and 110 g of acetic acid.

In the second experiment the reaction was continued for 45 minutes, the autoclave was cooled to room temperature and the pressure released.

The liquid product was removed from the autoclave and a small portion analysed by gas-liquid chromatography. This indicated that the following products were present in the reaction solution:- 117 g of acetic acid and only 33 g of formic acid.

This Example demonstrates the importance of limiting the extent of carbonylation of methyl formate in optimising the yield of formic acid.

I claim:

1. A process for the co-production of a $C_2$ to $C_{10}$ monocarboxylic acid and formic acid which process comprises reacting so that the conversion of the alkyl formate to carbonylation products is less than 90% at an elevated temperature below 250° C. a $C_1$ to $C_9$ alkyl formate with carbon monoxide and water in the presence as catalyst of a Group VIII noble metal component and an iodine or bromine-containing promoter, the molar ratio of water to alkyl formate is in the range of 1:1 to 10:1, the partial pressure of carbon monoxide being in the range 1 to 300 bar, the concentration of noble metal component being in the range from 100 to 5000 ppm and the atomic ratio of noble metal to iodine or bromine being in the range from 1:50 to 1:1000 and thereafter recovering the co-produced $C_2$ to $C_{10}$ monocarboxylic acid and formic acid.

2. A process according to claim 1 wherein the alkyl formate is methyl formate and the monocarboxylic acid co-produced with formic acid is acetic acid.

3. A process according to claim 2 wherein the ratio of formic acid to acetic acid in the recovered product is adjusted by addition of methanol to the reactants.

4. A process according to any one of the previous claims wherein the Group VIII noble metal component is a rhodium component.

5. A process according to claim 4 wherein the rhodium component is in the form of a halide, a carbonyl or a carboxylate.

6. A process according to claim 4 wherein the promoter is methyl iodide and/or hydrogen iodide.

7. A process according to claim 4 wherein a solvent which is the monocarboxylic acid produced in the reaction is employed.

8. A process according to claim 4 wherein the partial pressure of carbon monoxide is in the range 10 to 40 bar, the concentration of the noble metal compound is in the range from 300 to 1000 ppm, the atomic ratio of noble metal to iodine or bromine is in the range from 1:75 to 1:500 and the temperature is in the range 140° to 200° C.

9. A process according to claim 4 when operated continuously.

* * * * *

UNITED STATES PATENT AND TRADEMARK OFFICE
CERTIFICATE OF CORRECTION

PATENT NO. : 4,613,693
DATED : September 23, 1986
INVENTOR(S) : DAVID J.M. RAY

It is certified that error appears in the above-identified patent and that said Letters Patent is hereby corrected as shown below:

Col. 4, line 31, "sonoxide" should read --monoxide--

Signed and Sealed this

Twenty-seventh Day of January, 1987

Attest:

DONALD J. QUIGG

Attesting Officer  Commissioner of Patents and Trademarks